United States Patent [19]

Gladon et al.

[11] Patent Number: 4,653,641

[45] Date of Patent: Mar. 31, 1987

[54] PACKAGE CONTAINING AMINOOXYACETIC ACID (AOA) WITH INSTRUCTIONS FOR USE AS A PLANT GROWTH INHIBITOR

[75] Inventors: Richard J. Gladon; David S. Koranski, both of Ames, Iowa

[73] Assignee: Iowa State University Research Foundation, Inc., Ames, Iowa

[21] Appl. No.: 818,758

[22] Filed: Jan. 14, 1986

Related U.S. Application Data

[62] Division of Ser. No. 593,272, Mar. 26, 1984, Pat. No. 4,608,076.

[51] Int. Cl.$^4$ ............................................. B65D 85/82
[52] U.S. Cl. .................................. 206/459; 206/524.1
[58] Field of Search .................. 206/459, 524.1, 524.5; 71/76, 113

[56] References Cited

U.S. PATENT DOCUMENTS

| | | | |
|---|---|---|---|
| 2,644,259 | 7/1953 | Beadle | 206/459 |
| 3,255,871 | 6/1966 | Butler | 206/459 |
| 3,281,056 | 10/1966 | Kudler | 206/459 |
| 3,858,717 | 1/1975 | Peters | 206/459 |
| 4,247,563 | 1/1981 | Sample | 206/459 |

FOREIGN PATENT DOCUMENTS

692744 8/1964 Canada .............................. 206/459

OTHER PUBLICATIONS

Hoagland et al., Chem. Abst., vol. 97 (1982), 176987u.

*Primary Examiner*—William Price
*Assistant Examiner*—Brenda J. Ehrhardt
*Attorney, Agent, or Firm*—Zarley, McKee, Thomte, Voorhees & Sease

[57] ABSTRACT

A method of inhibiting plant height growth without having any significant impact on flowering, which comprises applying to the above ground portion of the plant at a point in time when the plant is beyond the seed leaf stage, and at least at approximately at the first true leaf stage, a small but growth inhibiting amount of aminooxyacetic acid.

1 Claim, No Drawings

PACKAGE CONTAINING AMINOOXYACETIC ACID (AOA) WITH INSTRUCTIONS FOR USE AS A PLANT GROWTH INHIBITOR

This is a division of application Ser. No. 593,272, filed Mar. 26, 1984 now U.S. Pat. No. 4,608,076.

BACKGROUND OF THE INVENTION

This invention relates to compositions and methods for controlling plant growth, particularly the growth of bedding plants. More particularly, it relates to compositions and methods for controlling the height of bedding plants.

It is desirable from time to time to control the height of bedding plants. The purchasing consumer does not necessarily regard a tall plant as aesthetically pleasing. It is, therefore, typical for commercial producers to apply a growth regulator to inhibit bedding plants from growing to an unusually tall size before they are sold. Typical of the growth regulators which have been used from time to time in the past are B-Nine (butanededic acid mono[2,2-dimethylethyldrazide]); A-Rest (alpha-cyclopropyl-alpha-[methoxyphenyl]-5-pyrmidinemethanol); Cycocel (2-[chloroethyl[trimethylammonium chloride); Florel (ethephon) (2-chloroethyl phosphonic acid).

While these prior art growth regulators all have some effect on some particular bedding plants, they do not have widespread general applicability to all types of bedding plants, such as petunias, impatiens, geraniums, pansies, snapdragons, and ageratums. Moreover, many of the above referred to prior art growth regulators are only effective for a short term delay in height growth, after which the plant continues growing taller. In addition, the activity of the above referred to prior art growth regulators commonly used for bedding plants are often temperature-dependent as to their effectiveness. This is particularly true for B-Nine.

Accordingly, it can be seen that there is a real and continuing need for an effective plant growth regulator of general applicability for bedding plants, which significantly delays, and in some cases actually stops, growth in height. This invention has as its primary objective the fulfillment of this need.

In addition, another objective of the present invention is to provide a plant growth regulator which, while delaying, retarding, and in some cases stopping plant height growth, has no significant impact whatsoever on the time until the plant flowers.

An even further objective of the present invention is to provide a method and composition for general applicability to bedding plants and potted flowering plants, which contains as its active ingredient, aminooxyacetic acid.

The method and manner of accomplishing each of the above objectives, as well as others, will become apparent from the detailed description which follows.

DETAILED DESCRIPTION OF THE INVENTION

While aminooxyacetic acid has been suggested in the past as possible inhibitor of ethylene biosynthesis in plants, see HortScience 1980, 15:238-243, and HortScience, 1981, 16:25-30, no one heretofore has ever appreciated that this relatively inexpensive compound can be an effective plant height growth regulator having widespread general applicability to bedding plants. Importantly, the use of aminooxyacetic acid also has no significant impact upon flowering of the plant. It merely retards plant height growth, which is, of course, a highly favorable effect.

Aminooxyacetic acid has the formula:

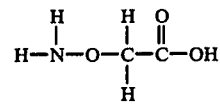

While it is possible that water soluble salts of aminooxyacetic acid will have the same desirable effect as aminooxyacetic acid itself, to date testing has only been limited to aminooxyacetic acid per se. Nevertheless, it is within the range of predictability that water soluble salts which are not harmful to the bedding plant would also be operable, particularly Group I and Group II metal water soluble salts of aminooxyacetic acid. It has been found in accordance with this invention that the timing of the application of the aminooxyacetic acid is also an important aspect of the invention. In particular, in order to maximize inhibition of plant growth, while at the same time having no significant impact on plant flowering, the aminooxyacetic acid should be applied directly to the exterior of the plant when the plant is beyond its cotyledon or in other words, "seed leaf" stage. Next beyond the "seed leaf stage" is what is commonly referred to as "the number one stage", or in other words, the first true leaf stage. The optimum time for application is from about the first to the third true leaf stage. Most preferred is the second true leaf stage. It may be used at a higher number of true leaves, if desired.

The most effective form for the aminooxyacetic acid is a water solution, and most preferably a water solution containing a wetting agent such as Tween 20 or Triton X100 at a level of from about 0.05% to about 0.1% by weight of the wetting agent. Having wetting agents in the water solution are desirable because this allows for better coverage on the leaf, or in other words, the active ingredient is allowed to spread more evenly and effectively over the surface of the whole leaf. The precise wetting agent is not critical, so long as it is effective and not harmful to the leaf.

The concentration of active aminooxyacetic acid ingredient to provide the desired plant height growth inhibition should be from about 1 millimolar to about 24 millimolar, preferably from about 4 to about 16 millimolar. The preferred technique of application is to spray to run off. For impatiens, the concentration should not exceed 12 millimolar. However, both the preparation form of the active ingredient and its application form may be any suitable conventional one. The preferred preparation form is, of course, liquid preparations containing one or more surface active or wetting agents.

The following examples are offered to further illustrate but not limit the invention disclosed and clearly demonstrate the effectiveness of aminooxyacetic acid in inhibiting plant height growth.

EXAMPLE 1

In this and the following experiments as well, a water solution of aminooxyacetic acid containing 0.1% of a wetting agent sold under the mark Tween 20 and/or Triton X100, was simply sprayed to run off upon the above ground portions of the below-described plants at the number 1 stage, that is, the first true leaf stage. The concentrations were as specified in each example below, and spray-on was accomplished with a conventional compression atomizer. The plants were all positioned in conventional plastic pots, 10 to 11 centimeters in diameter, and growing in a typical potted plant soil mixture. Cultivation was carried out in a greenhouse unless otherwise specified.

TABLE 1

The effect of aminooxvacetic acid on controlling the height of petunias grown from plug flats

|  | Control (0 mM) | 8 mM 1* | 8 mM 2* | 16 mM 1* | 16 mM 2* |
|---|---|---|---|---|---|
| Height$^x$ (centimeters) | 13.2 | 9.5 | 8.2 | 8.3 | 7.4 |
| Days to flowering$^x$ | 67 | 64 | 66 | 65 | 67 |

*Number of applications (10 days apart)
$^x$Mean (50 plants per treatment)

From the above, it can be seen that the average height of the plants treated with the active ingredient was significantly reduced. Correspondingly, the days to flowering were not significantly changed. It is, therefore, shown from the data that aminooxyacetic acid is an effective plant growth regulator for controlling the height of petunias grown from plug flats.

EXAMPLE 2

The aminooxyacetic acid formulation and method of application were as described in Example 1. The plants were petunia 'White Flash' grown in the fall. The results are shown in the following table. It can be seen that height was satisfactorily controlled at levels of application within the range of from about 8 mM per milliliter to about 16 mM.

TABLE 2

The effect of aminooxyacetic acid on Petunia "White Flash" grown in the Fall

|  | Control (0 mM) | 4 mM | 8 mM | 12 mM | 16 mM |
|---|---|---|---|---|---|
| Height$^z$ | 6.9 | 6.8 | 4.5 | 4.0 | 2.5 |
| Days to flowering$^z$ | 66 | 67 | 68 | 65 | 66 |

$^z$Mean (12 plants/treatment).

EXAMPLE 3

The effect of AOA on height retardation of Petunia 'White Flash' grown in the spring was measured. The concentration and liquid composition of the active aminooxyacetic acid was as described in example 1. Table 3 shows the results of the study.

TABLE 3

The effect of aminooxyacetic acid on height retardation of Petunia White Flash grown in the Spring

|  | 2 mM 1* | 2 mM 2* | 2 mM 3* | 4 mM 1* | 4 mM 2* | 4 mM 3* | 8 mM 1* | 8 mM 2* | 8 mM 3* |
|---|---|---|---|---|---|---|---|---|---|
| Height** | 15.9 | 12.9 | 12.0 | 12.4 | 11.1 | 11.0 | 13.7 | 9.9 | 6.4 |
| Days to flowering$^y$ | 67 | 65 | 68 | 68 | 66 | 64 | 67 | 65 | 67 |

|  | 12 mM 1* | 12 mM 2* | 12 mM 3* | 16 mM 1* | 16 mM 2* | 16 mM 3* |
|---|---|---|---|---|---|---|
| Height** | 11.3 | 9.3 | 5.3 | 10.0 | 10.0 | 7.8 |
| Days to flowering$^y$ | 64 | 66 | 68 | 63 | 65 | 66 |

|  | Control H$_2$O | H$_2$O + HCl (1 appl.) | H$_2$O + HCl (1 appl.) |
|---|---|---|---|
| Height$^y$ | 14.1 | 12.8 | 13.2 |
| Days to flowering | 67 | 65 | 65 |

*Number of applications applied at 10 day intervals.
**Height in centimeters
$^y$Mean (10 plants per treatment)

The data in the table show that AOA, when compared to the control, showed effective height retardation of Petunia 'White Flash' grown in the spring.

From the data shown in Examples 1 through 3 on petunia, it can be seen that aminooxyacetic acid is an effective plant height growth inhibitor for petunias and that it does not have any significant impact or delay on flowering.

The following Table 4 shows treatment of impatiens with a spray to run off of the composition and at the second true leaf stage.

TABLE 4

The effect of AOA in controlling height, diameter, and days to flower of impatiens 'Super Elfin Scarlet' grown in the fall.

| mM AOA | Number of Applications$^z$ | Height$^y$ (mM) | Diameter$^y$ (mM) | Days to Flower |
|---|---|---|---|---|
| 0 | 1 | 34.39 | 69.64 | 75 |
| 4 | 1 | 33.44 | 38.44 | 84 |
|  | 2 | 27.50 | 37.92 | 85 |
|  | 3 | 22.46 | 36.34 | 87 |
| 8 | 1 | 29.17 | 40.27 | 84 |
|  | 2 | 22.20 | 37.11 | 87 |
|  | 3 | 24.28 | 29.41 | 85 |
| 12 | 1 | 13.84 | 48.47 | 89 |
|  | 2 | 15.94 | 39.71 | 90 |
|  | 3 | 10.61 | 19.11 | 93 |

$^z$Number of applications applied at 7-day intervals.
$^y$Mean (18 plants per treatment)

What is claimed is:

1. As a bedding plant growth inhibitor, in combination finely divided aminooxyacetic acid, a package surrounding said aminooxyacetic acid, and package instructions, instructing height growth inhibition of said plants by spraying on the plant leaves of bedding plants a water soluble solution of aminooxyacetic acid to the point of run-off at at least the first true leaf stage, at a solution concentration of from about 1 millimolar to about 24 millimolar.

* * * * *